United States Patent [19]
Delpuech et al.

[11] Patent Number: 5,185,099
[45] Date of Patent: Feb. 9, 1993

[54] VISCO-ELASTIC, ISOTROPIC MATERIALS BASED ON WATER, FLUORINATE SUFACTANTS AND FLUORINATED OILS, PROCESS FOR THEIR PREPARATION, AND THEIR USE IN VARIOUS FIELDS, SUCH AS OPTICS, PHARMACOLOGY AND ELECTRODYNAMICS

[75] Inventors: Jean-Jacques Delpuech, Laxou; Louis Matos, Vandoeuvre; El Mostafa Moumni, Villers; Jean-Claude Ravey, Messein; Claude Selve, Villers les Nancy; Guy Serratrice, Crolles; Marie-José Stébé, Vandoeuvre les Nancy; Aimé Cambon, Nice; Gérard Thiollet, Cerny, all of France

[73] Assignee: Institut National de Recherche Chimique Appliquee, Paris, France

[21] Appl. No.: 794,375

[22] Filed: Nov. 14, 1991

Related U.S. Application Data

[63] Continuation of Ser. No. 340,621, Apr. 19, 1989, abandoned.

[30] Foreign Application Priority Data

Apr. 20, 1988 [FR] France ................................ 88 05229

[51] Int. Cl.$^5$ ............................................. B01J 13/00
[52] U.S. Cl. .................................. 252/315.1; 252/312; 252/315.01
[58] Field of Search ................. 252/315.1, 315.01, 312

[56] References Cited

U.S. PATENT DOCUMENTS 4,569,784  2/1986  Moore ............................. 252/315.1
4,879,062  11/1989  Moore ............................. 252/315.1

FOREIGN PATENT DOCUMENTS 051526  5/1982  European Pat. Off. .
2249657  5/1975  France .
2087882  6/1982  United Kingdom .

OTHER PUBLICATIONS

Chemical Abstracts, vol. 83, No. 1, Jul. 14, 1975, p. 349, No. 15661d, Columbus, Ohio, US; & JP-A-73 123 184 (Asahi Denka Kogyo K.K. 25-Nov. 25, 1974 Resume).
Journal of Colloid and Interface Science, vol. 98, No. 2, Apr. 1984, pp. 515-522, Academic Press, Inc.; A. Robert et al.: "Solubilization of water in binary mixtures of fluorocarbons and nonionic fluorinated surfactants: Existence domains of reverse emulsions" pp. 515-522.
Journal of the American Chemical Society, vol. 106, No. 21, 1984, pp. 6162-6171, American Chemical Society; G. Mathis et al "A novel class of nonionic microemulsions: Fluorocarbons in aqueous solutions of fluorinated poly(oxyethylene) surfactants" Resume; pp. 6167-6171.

Primary Examiner—Robert L. Stoll
Assistant Examiner—Philip Tucker
Attorney, Agent, or Firm—Browdy and Neimark

[57] ABSTRACT

These materials having the appearance and the consistency of gels are characterized in that they contain a very high proportion of water, of the order of from 60 to 98% weight, and that their structure is a microcellular compartmentalized structure having a very high density of water droplets enclosed in a fine surfactant membrane and contained in a continuous oil/surfactant phase, this structure being impermeable to water and permeable to hydrophobic compounds soluble in fluorocarbons.

Use in the field of optics, fillers, cosmetics, pharmacology, lubricants, textiles, photochemistry and electrodynamics.

7 Claims, No Drawings

VISCO-ELASTIC, ISOTROPIC MATERIALS BASED ON WATER, FLUORINATE SUFACTANTS AND FLUORINATED OILS, PROCESS FOR THEIR PREPARATION, AND THEIR USE IN VARIOUS FIELDS, SUCH AS OPTICS, PHARMACOLOGY AND ELECTRODYNAMICS

This application is a continuation of application Ser. No. 07/340,621, filed Apr. 19, 1989, now abandoned.

FIELD OF THE INVENTION

The present invention relates to transparent isotropic visco-elastic materials based on fluorinated surfactants and fluorinated oils containing a very high proportion of water of the order of 60 to 98% by weight.

In the present description it is to be understood that "visco-elastic materials" means materials which are simultaneously viscous and elastic and which have the appearance and the consistency of "gels"; which term, for the sake of convenience, will be used to describe them hereafter.

The fluorinated surfactants used in these materials are more precisely non-ionic surfactants with an essentially fluorinated hydrophobic chain.

As well as having a very high content of water, the gels according to the invention belong to a quite particular category, distinct from the gels conventionally called hydrogels.

BACKGROUND OF THE INVENTION

In fact, different classes of hydrogels are known depending on the chemical or physical structure of the latter. An often used classification, especially in the biomedical field, distinguishes between neutral or non-ionic hydrogels (of the cellulose type, for example), ionic hydrogels (of the silicate type, for example) and interpenetrated polymeric networks (IPN). These known hydrogels generally have water-swollen networks (crosslinked structures) of hydrophilic polymers or copolymers. These networks are three-dimensional and the crosslinkings are formed by covalent or ionic bonds Frequently weaker bonds of the Van der Waals type, or hydrogen bond, can serve as crosslinks thus forming the swollen networks which behave as hydrogels.

Finally, semi-crystalline and un-crosslinked hydrophilic polymers can form hydrogels by swelling then the crystallites act as physical crosslinks, it being understood that they do not dissolve in water, unlike amorphous constituents.

SUMMARY OF THE INVENTION

The gels according to the present invention are differentiated from existing hydrogels by their structure which is a "compartmentalized" structure, that is to say a structure which, viewed under an electron microscope, has a very strong density of water droplets enclosed in a fine surfactant membrane and contained in a continuous oil/surfactant phase. The properties of the surfactant(s) forming part of this structure influence the behaviour of the resulting "gels" with respect to water and oil as they have a net impermeability to water and permeability to hydrophobic compounds soluble in fluorocarbons, in particular gases (for example respiratory gases) and fluorinated or even hydrogenated compounds which are not too fluorophobic. Such a result can be obtained with non-ionic surfactants having an essentially fluorinated hydrophobic part and relatively low hydrophilic properties and therefore advantageously having an appropriate hydrophilic lipophilic balance, or hlb calculated according to the Griffin formula at less than 8 and preferably lying between 4 and 6.

The subject of the present application is therefore isotropic visco-elastic materials based on water, fluorinated surfactants and fluorinated oils having the appearance and the consistency of gels, characterized in that they contain a very high proportion of water, of the order of 60 to 98% by weight, and that their structure is a microcellular compartmentalized structure having a very high content of water droplets enclosed in a thin surfactant membrane and contained in a continuous oil/surfactant phase, said structure being impermeable to water and permeable to hydrophobic compounds soluble in flourocarbons.

According to other features:

the water droplets forming part of the structure of the materials according to the invention have an average size of about the order of a micron;

the materials, prepared with salt-containing water, have a very low electrical conductivity, of the order of a few tenths of a microsiemens/cm.

The isotropic visco-elastic materials according to the invention are also characterized by the combination of the following other physical properties: transparency, surfactant character chemically inert, stability, permeation properties.

The preferred materials are those characterized in that the fluorinated surfactants are non-ionic surfactants with an essentially fluorinated chain, and that the fluorinated oils are selected from fully or partially fluorinated hydrocarbons containing at least 6 carbon atoms, preferably from 6 to 20 carbon atoms, and in particular about 10 carbon atoms.

As surfactants with basically fluorinated hydrophobic bonds used in the invention, the following can in particular be cited products of the type:

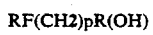 RF(CH2)pR(OH) (Family 1)

where p is generally less than 3, in which RF is a perfluorinated bond, and R means a chain of oxyethylene (OC2H4) units, where one or more oxygen atoms can be replaced by sulphur atoms.

The products of this family where p=2 are notably described in French Patent No. 2,565,226.

products of the type:

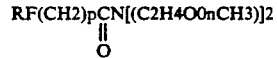

RF(CH2)pCN[(C2H4OOnCH3)]2 (Family II)
‖
O where p is generally less than 3.

Products of this family where p=1 or p=0 are described in French Patent Application No. 87-06515;

as well as all surfactant products with fluorinated chain(s) having relatively low hydrophilic properties, characterized by a HLB, calculated according to the Griffin formula, of less than 8, associating a hydrophilic part containing poloxyethylene —(OC2H4)n-groups where n<2, with a fluorinated hydrophobic part containing —$C_xF$2x—units where 4<x<12.

As fluorinated oils to be used in the ternary mixtures according to the invention, there can in particular be mentioned fully or partly fluorinated hydrocarbons typically containing 6 to 20 carbon atoms, in particular hydrocarbons having 10 carbon atoms, and optionally containing branches, unsaturations, aliphatic or aromatic rings and hetero-atoms.

It is to be noted that direct mixture of the three constituents in the poportions corrsponding to the final composition of the gel is not necessarily conducive to easy preparation of this gel. An important variant of the preparative process involves preliminary pre-mixture passing through the stage of a clear/transparent isotropic medium the viscosity of which is then increased in an unexpected manner by the progressive addition of water.

The gels according to the invention can also be obtained by replacing the water by a mixture of water and a water-miscible solvent, for example by a water-DMSO or water-propyleneglycol mixture, or by an homogenous aqueous solution having one or more solutes dissolved therein, for example an ionic solution or a cell culture medium, or a polymerizable substance, for example an acrylate.

Similarly, the gel according to the invention in one or the other of its phases (water or oil), or even in both, can contain any desired substances having an activity appropriate for the use(s) envisaged for the gel containing them.

The present invention accordingly also embraces the uses, which as will be understood are directly linked to the physical properties of the products in question, namely:

transparency of the gels thus obtained, notably of those obtained from water, fluorinated oil and non-ionic surfactant; in fact, the refractive index of the products being near that of water, the hydrogels thus obtained are perfectly transparent, an essential property for optical or photochemical uses;

visco-elasticity which can be modified as a function of the proportion of the constituents: these products in fact take the form of an easily handled gel.

Their apparent viscosity can vary within wide limits, depending on the quantity of water incorporated, the nature of the surfactant and the temperature. Gels of a high rigidity are obtained with high concentrations of water (90-98% by weight), whereas relatively mobile gels are obtained with lower concentrations of water (70-90%), thus making them more suitable for use in cavities as filling materials. Their rheological behaviour is of the "plastic" type, that is to say that spreading them out necessitates the use of a minimal force above a threshold which depends on the composition of the gel. As an example of this threshold, for a gel based on perfluorodecalin, on $C_6F_{13}C_2H_4S(C_2H_4O)_3H$ and on water is approximately 16 $N/m^2$ when the gel contains 80% water, and is approximately 35 to 40 $N/m^2$ when the gel contains 90% water;

surfactant character: the previous handlings are again made possible by the fact that these gels have a high surface wetting power as they are constituted starting from fluorinated surfactants, which is a valuable property for numerous uses in formulation (for example cosmetics). These fluorinated surfactants introduce an effect enabling them to flow and spread out exceptionally well, an effect sought after in numerous applications (lubrication, film-formation, textiles);

chemical inertness: the high fluorine content imports a stable character to the products used in the compositions of the gels: notably thermal stability up to 100° C., in particular from 10° to 60° C., resistance to oxidation notably to strong oxidising agents such as potassium permanganate or chromium salts, to hydrolysis and to the action of the usual chemical or biochemical agents such as citric acid, nitric acid, hydrochloric acid and the hydracids in general, bases such as potassium hydroxide or sodium hydroxide and to strong or weak bases in general, while the products are not substrates for enzymes and in particular are not substrates for proteases;

stability: the stability of the gels of the present invention varies inversely with the quantity of water present in the mixture. Thus, as regards the fractions with a water-mass lower than 90-98%, the gels are very stable; only after a few days does a fine layer of water appear at the surface of the gel, without its losing its initial consistency. On the other hand, when the quantity of water reaches 98%, a layer of water appears more quickly which tends to increase with time.

However, the layer of exuded water can be re-incorporated by simple agitation, restoring its initial consistency to the gel.

Of course, the stability varies with temperature and the water content. Electrolytes or molecular solutes can be added in moderate quantities (of the order of a mole per liter) to these gels, either in the aqueous phase or in the phase constituting the boundaries of the compartments (fluorocarbon+surfactant) without destroying them: their zone of existence is simply displaced in terms of temperature.

impermeability; especially to water, and permeability, particularly to fluorinated oils.

The present invention also relates to a process for obtaining the visco-elastic materials in question.

This process consists in particular of bringing together the fluorinated oil, the fluorinated surfactant and the necessary and sufficient quantity of water to obtain a clear isotropic pre-mixture, and then progressively to add water to this until the desired gel is obtained.

In order to find the clear isotropic pre-mixture zone, one can for example prepare a ternary diagram of the selected constituents.

There exists a great flexibility of formulation, which makes it possible, as desired to obtain transparent and stable gels in a temperature zone between ambient temperature and 80° C., by adjusting in an interdependent way the hydrophilic properties of the surfactant, the presence of solutes in the water, the fluorocarbon/surfactant mass relationship, and the nature of the oil. In particular, an increase in temperature has the same effect as a decrease of HLB. The hydrophilic properties of the surfactant can be regulated as desired either by changing the surfactant, or by making mixtures of surfactants of different HLB. A final, more subtle means of changing the temperature zone consists in varying the isotopic composition of the water:

an increase in temperature which can be as much as 20° C. is observed upon substituting heavy water (D20) for light water (H20), the intermediate variants being found by using H20/D20 mixtures of variable isotopic ratio.

Finally the completely original compartmentalized structure of these hydrogels, which in particular is different from that of hydrogels known till now, makes it possible to envisage different uses: thus it is possible to produce aqueous ionic media which are feebly conductive for electric current, and thus rather special dielectrics with strong polarization. The compartmentalization makes it possible to obtain mixed gels charged with ions usually incompatible with each other, because of either precipitation or oxidation/reduction phenomena.

In general, this compartmentalized structure can make it possible to achieve chemical reactions in a confined medium. A classic example is the preparation of finely-divided solid materials, which are powdery or alternatively in the form of a mousse, by the photochemical polymerization in situ of a hydro or flurosoluble monomer.

Encapsulation properties, similar to those of vesicles (with less stability but on the other hand with a greater facility of preparation and of reversibility), can be foreseen in such systems, making for numerous uses or formulations, in particular in pharmacology.

For the same reasons, the permeation properties result from this compartmentalized structure: impermeability to water and to ionic/aqueous solutions and permeability to hydrophobic compounds soluble in fluorocarbons, notably gases (for example the respiratory gases) and fluorinated or even hydrogenated compounds which are not too fluorophobic. The potential uses for these permeation properties therefore relate to the field of chromatography in all its forms, to the preparation of chemically-inert semi-permeable membranes, and to application as carriers in pharmacy (cicatrizant ointments because permeable to oxygen and to carbon dioxide) or in opthalomology.

Finally, the subject of the present application includes the use of the materials as defined above in the field of optics, filling materials, cosmetics, pharmacology, lubricants, textiles, photochemistry and electrodynamics.

DETAILED DESCRIPTION OF THE INVENTION

Examples of the present invention are offered in an illustrative and non-limiting capacity.

1. EXAMPLES OF THE PREPARATION OF THE GELS ACCORDING TO THE INVENTION

General Mode of Procedure

A solution is made up from a defined quantity of surfactant (n) and a defined quantity of the selected perfluorinated oil (p).

To this solution there is added the aqueous solution in defined quantities (m) while homogenizing by agitation and heating until the selected proportions are reached.

EXAMPLE 1

72.1% water—5.2% surfactant and 22.7% perfluorodecalin: to a solution where n=10.4 mg of $C_{10}F_{21}CH_2C(O)N[C_2H_4O)_2ME]_2$ and p=45.4 mg of perfluorodecalin, following the mode of procedure descibed above, m=144,2 mg of water is added. The gel obtained is stable upwards from 10° C. and remains stable at 60° C.

EXAMPLE 2

81% water—4% surfactant and 15% of perfluorodecalin to a solution where n=16 mg of $C_{10}F_{21}CH_2C(O)N[(C_2H_4O)_2Me]_2$ and p=60 mg of perfluorodecalin, one adds m=324 mg of water following the general mode of procedure described above. The gel obtained is stable upwards from 10° C. and remains stable at 60° C.

EXAMPLE 3

90% of water—0.7% of surfactant and 2.3% perfluorodecalin: to a solution of n=7 mg of $C_{10}F_{21}CH_2C(O)N[(C_2H_4O)Me]_2$ and p=23 mg of perfluorodecalin, one adds m=970 mg of water following the mode of operation described above. The gel obtained is stable upwards from 10° C. and remains stable at 60° C.

EXAMPLE 4

97% of water—0.6% of surfactant and 2.4% of perfluorodecalin: to a solution where n=6 mg of $C_6F_{13}C_2H_4S(C_2H_4O)_3H$ and p=24 mg of perfluorodecalin, one adds m=970 mg of water following the general mode of procedure described above. The gel obtained is transparent and stable between 20° and 30° C.

EXAMPLE 5

90% of water—4% of surfactant—6% $C_4F_9CH=CHC_4F_9$: to a solution where n=40 mg of $C_6F_{13}C_2H_4S(C_2H_4O)_3H$ and p=60 mg of $C_4F_9CH=CHC_4F_9$, one adds m=900 mg of water following the general mode of procedure described above. The gel obtained is transparent and stable between 20° and 30° C.

EXAMPLE 6

90% of water—2.3% surfactant—7.7% $C_8F_{17}CH=CH_2$: to a solution where n=23 mg of $C_6F_{13}C_2H_4S(C_2H_4O)_2C_2H_4S(C_2H_4O)_3H$ and p=77 mg of $C_8F_{17}CH=CH_2$, one adds m=900 mg of water. The gel obtained is transparent and stable between 20° and 30° C.

EXAMPLE 7

90% water—3.5% surfactant—6.5% $C_8F_{17}CH=CH_2$: to a solution where n=35 mg of $C_6F_{13}C_2H_4S(C_2H_4O)_3H$ and p=65 mg of $C_8F_{17}CH=CH_2$, one adds m=900 mg of water. The gel obtained is transparent and stable between 20° and 30° C.

EXAMPLE 8

81% water—4% surfactant—15% $C_8F_{17}CH=CH_2$: to a solution where n=40 mg of $C_6F_{13}C_2H_4SC_2H_4SOC_2H_4S(C_2H_4O)_3H$ and p=150 mg of $C_8F_{17}CH=CH_2$, one adds m=180 mg of water. The gel obtained is transparent and stable between 20° and 30° C.

EXAMPLE 9

88% water—4% surfactant—8% $C_8F_{17}CH=CH_2$: to a solution where n=40 mg of $C_6F_{13}C_2H_4S(C_2H_4O)_4H$ and p=80 mg of $C_8F_{17}CH=CH_2$, one adds m=880 mg of water. The gel obtained is transparent and stable between 20° and 30° C.

EXAMPLE 10

90% water—1.8% surfactant—8.2% perfluorodecalin: to a solution where n=18 mg of $C_6F_{13}C_2H_4S(C_2H_4O)_4H$ and p=82 mg of perfluorodecaline, one adds m=900 mg of water. The gel obtained is transparent and stable between 20° and 30° C.

EXAMPLE 11

85.8% water—4.4% surfactant—9.3% perfluorodecalin: to a solution of 44.0 mg of $C_6F_{13}CH_2(OCH_2CH_2)_3OH$ and 82.5 mg of perfluorodecaline, one adds 764.0 mg of water. The gel obtained is transparent and stable between approximately 15° and 28° C.

EXAMPLE 12

74.0% water—8.5% surfactant—17.5% perfluordecalin to a solution of 50.0 mg of $C_6F_{13}CH_2(OCH_2CH_2)_3OH$ and 102.5 mg of perfluorodecalin, one adds 434.0 mg of water. The gel obtained is transparent and stable between 20° and 30°.

EXAMPLE 13

71.7% water—12.1% surfactant—16.2% perfluorodecalin: to a solution of 72.6 mg of $C_6F_{13}CH_2(OCH_2CH_2)_3OH$ and 97.2 mg of perfluorodecalin, one adds 430.2 mg of water. The gel obtained is transparent and stable at around 40° C.

EXAMPLE 14

54.1% water—13.7% surfactant—32.1% perfluorodecalin: to a solution of 41.8 mg of $C_6F_{13}CH_2(OCH_2CH_2)_4OH$ and 98.0 mg of perfluorodecalin, one adds 165.1 mg of water. The gel obtained is transparent and stable at 50° C.

EXAMPLE 15

87.3% water—3.8% surfactant—8.9% oil: to a solution of 11.4 mg of $C_6F_{13}CH_2(OCH_2CH_2)_4OH$ and 26.7 mg of perfluorodecalene, one adds 261.9 mg of water. The gel obtained is transparent and stable at 38° C.

EXAMPLE 16

81% water/DMSO (v/v), 3% surfactant and 16% perfluorodecalin: to a solution where n=30 mg of $C_{10}F_{21}CH_2C(O)N[(C_2H_4O)_2Me]_2$ and where p=160 mg of perfluorodecalin, one adds m=810 mg of an aqueous phase [consisting of a solution of 1 volume of water, 1 volume of dimethylsuloxide (DMSO)] following the general mode of procedure described above. The gel obtained is stable upwards from 10° C. and remains stable at 40° C.

EXAMPLE 17

81% water-propyleneglycol (v/v), 3% surfactant and 16% perfluorodecaline: the same composition as that in Example 16 is prepared following the general mode of procedure using a solution consisting of 1 volume of water and 1 volume of propylene-glycol as the aqueous phase. The gel obtained has the same stability as that of Example 16.

EXAMPLE 18

A gel with a composition identical to that in Example 4, but prepared with an aqueous phase consisting of water in which 10 g/liter of NaCl is dissolved, has a temperature zone of optimum stability, which ranges from 15° to 25° C. (A decrease of 4° C. in for the optimum stability zone is observed).

EXAMPLE 19

A gel with a composition identical to that in Example 4, but prepared with heavy water (D$_2$O instead of H$_2$O) has a temperature zone of optimum stability which extneds from 45° to 55° C. (A displacement of +25° C. in the optimum stability zone is observed).

EXAMPLE 20

A gel with a composition identical to that in Example 4, but prepared with an aqueous phase consisting of a solution of 60 g of sodium chloride (NaCl) in heavy water (D$_2$O) has a temperature zone of optimum stability, identical to that of the gel in Example 4.

EXAMPLE 21

77% water, 5% surfactant (artificial mixture and made up of two surfactants), 18% of perfluorodecalin: to a solution where n=n1+n2, where n1=12.5 mg of $C_6F_{13}C_2H_4S(C_2H_4O)_3H$ and where n2=12.5 mg of $C_6F_{13}C_2H_4S(C_2H_4O)_4H$, one adds p=90 mg of perfluorodecalin and m=385 mg of water. The gel obtained following the general mode of procedure is stable between 25° and 35° C.

EXAMPLE 22

97.5% water, 1.7% $C_8F_{17}CH=CH_2$, 0.8% surfactant: to a solution of 1 g of $C_6F_{13}C_2H_4S(C_2H_4O)_3H$ and 2.1 g of $C_8F_{17}CH=CH_2$, one adds 120 g of water The gel obtained is transparent and stable between 18° and 30° C.

EXAMPLE 23

96.1% water, 2.68% $C_8F_{17}CH=CH_2$, 1.28% surfactant: to a solution of 1 g of $C_6F_{13}C_2H_4S(C_2H_4O)_3H$ and 2.1 g of $C_8F_{17}CH=CH_2$, one adds 75 g of water The gel obtained is transparent and stable between 18° and 30° C.

EXAMPLE 24

94.16% water, 3.95% $C_8F_{17}CH=CH_2$, 1.88% surfactant: to a solution of 1 g of $C_6F_{13}C_2H_4S(C_2H_4O)_3H$ and 2.1 g of $C_8F_{17}CH=CH_2$, one adds 50 g of water The gel obtained is transparent and stable between 18° and 30° C.

EXAMPLE 25

90.6% water, 6.35% $C_8F_{17}CH=CH_2$, 3.02% surfactant: to a solution of 1 g of $C_6F_{13}C_2H_4S(C_2H_4O)_3H$ and 2.1 g of $C_8F_{17}CH=CH_2$, one adds 30 g of water The gel obtained is transparent and stable between 18° and 30° C.

2. EXPERIMENTS ILLUSTRATING CERTAIN PROPERTIES OF THE GELS

Diffusion Between Gel and Water

A coloured aqueous solution of bromophenol (pinky-red colour) is put on the gels from Example 3 (97% water, 0.7% surfactant and 2.3% perfluorodecalin) and from Example 4 (97% water, 0.6% surfactant and 2.4% perfluorodecalin) and left to stand (without aqitation) at 25° C.; after 8 days, no coloration of the fluogel part could be observed. The same experiment, carried out by replacing the gels according to the invention by an aqueous agar-agar gel, showed complete coloration after 24 hours to a depth of 2 cm.

Diffusibility Between the Gel and the Fluorinated Oil.

(a) Approximately 1 ml of perfluorodecalin saturated with iodine was "put" on 1 ml of gel constituted following Example 2 (81% water, 4% $C_{10}F_{21}CH_2CON/[C_2H_4O)_2Me]2$, 15% of perfluorodecalin. After approximately two hours at rest, the gel is colored yellow by the iodine.

(b) If perfluorodecalin, saturated with iodine, is put on the gel, the respective densities of the perfluorodecalin phase and the gel being dpF>dgel, the gel can be seen to "cut up" into pieces which goes through the perfluorodecalin phase and finally the gel phase goes totally through without any apparent change in the respective quantities of the gel and of the perfluorodecalin; here again, the gel becomes yellow in colour.

(c) The same observations have been made with the gels from Example 10 and Example 12.

Conductivity

A step was carried out on a mixture made of 74% of water (with NaCl added at 0.5 g/l), 9% of $C_6F_{13}C_2H_4S(C_2H_4O)_3H$ sufactant and 17% of $C_8F_{17}CH=CH_2$.

The specific conductivity is then 0.46 uS.cm$^{-1}$, a very weak value in comparison to that of 0.5 g/l salt-containing water (946 uS.cm$^{-1}$ at 25° C.).

It goes without saying that the present invention has only been described in a purely illustrative and non-limiting manner and that all modifications, in particular with regard to technical equivalents, can be used without going outside the scope of the invention.

We claim:

1. Viscoelastic materials having the apperance and consistency of gels comprising fluorinated surfactants, fluorinated oils, and a solvent composition selected from the group consisting of water and mixtures of water and a water-miscible solvent, said materials containing from 60 to 98% by weight of water;

wherein a continuous phase of said materials comprises a mixture of said fluorinated surfactants and said fluorinated oils;

wherein said surfactant is a nonionic surfactant selected from the group consisting of (1) compounds of the formula $R_F(CH_2)_pR(OH)$ wherein p is less than 3, $R_F$ is a perfluorinated carbon chain, and R represents a chain of $(OC_2H_4)$ units, in which at least one oxygen atom is optionally replaced by a sulfur atom; and (2) compound of the formula

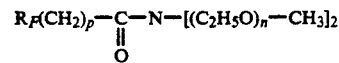

wherein p is less than 3; and (3) surfactants having an HLB, according to the Griffin formula, of less than 8, comprising a hydrophilic group containing $O(C_2H_4)_n$ groups wherein n>2 and a fluorinated hydrophobic group RF containing $(C_xF2_x)$ groups wherein 4<x<12.

2. Visco-elastic materials according to claim 1 wherein the structure of said viscoelatic materials is a microcellular compartmentalized structure having a very high density of droplets containing solvent compositions.

3. Viscoelastic materials according to claim 1 wherein said droplets have a size on the order of one micron.

4. Viscoelastic materials according to claim 1 wherein said solvent composition is a mixture of water and a water-miscible solvent selected from the group consisting of dimethylsulfoxide and propylene glycol.

5. Viscoelastic materials according to claim 1 having an electrical conductivity of about 0.46 μS/cm.

6. Viscoelastic materials according to claim 1 wherein the hydrophilic-lipophilic balance is less than 8.

7. Viscoelastic materials according to claim 6 wherein the hydrophilic-lipophilic balance is from 4 to 6.

* * * * *